US012562240B2

(12) United States Patent
Vuu et al.

(10) Patent No.: US 12,562,240 B2
(45) Date of Patent: Feb. 24, 2026

(54) POLLUTION TYPE SENSING

(71) Applicant: Wynd Technologies, Inc., San Jose, CA (US)

(72) Inventors: Jason Duy Vuu, San Jose, CA (US); Igor Reznichenko, King City, OR (US); Eric Munoz, South San Francisco, CA (US); Raymond Rui Wu, Millbrae, CA (US); Mengheng Touch, Reno, NV (US)

(73) Assignee: Wynd Technologies, Inc., San Jose, CA (US)

( * ) Notice: Subject to any disclaimer, the term of this patent is extended or adjusted under 35 U.S.C. 154(b) by 549 days.

(21) Appl. No.: 17/525,571

(22) Filed: Nov. 12, 2021

(65) Prior Publication Data

US 2022/0157408 A1 May 19, 2022

Related U.S. Application Data

(60) Provisional application No. 63/113,218, filed on Nov. 13, 2020.

(51) Int. Cl.
*G16C 20/70* (2019.01)
*G01N 21/94* (2006.01)
*G01N 33/00* (2006.01)

(52) U.S. Cl.
CPC ............. *G16C 20/70* (2019.02); *G01N 21/94* (2013.01); *G01N 33/0037* (2013.01); *G01N 33/004* (2013.01); *G01N 33/0047* (2013.01)

(58) Field of Classification Search
CPC ...... G16C 20/20; G16C 20/30; G01N 1/2273;

G01N 15/02; G01N 15/06; G01N 15/075; G01N 15/0205; G01N 2015/0222; G01N 15/1459; G01N 21/53; G01N 21/94; G01N 21/88; G01N 30/8637; G01N 30/8693; G01N 30/86; G01N 33/0037; G01N 33/004; G01N 33/0047; G01N 33/0075; G01N 33/0027; G01N 33/0036; G01N 2001/021; G01N 2021/945; G01N 2015/1493; G01N 2035/00881; G06N 3/08; G01B 11/28; G01J 1/00; G01W 1/02

See application file for complete search history.

(56) References Cited

U.S. PATENT DOCUMENTS 10,139,384 B1 * 11/2018 Nourbakhsh ...... G01N 33/0075
10,345,216 B2 * 7/2019 Clayton ................... C12Q 3/00
(Continued)

*Primary Examiner* — Lisa M Caputo
*Assistant Examiner* — Eric Sebastian Von Wald
(74) *Attorney, Agent, or Firm* — Scale LLP

(57) ABSTRACT

Systems and methods classify pollutants based on multifactor analysis of data from sensors in a monitored area and contextual data from remote or local sources. Classifying a pollutant in air at a monitored area may include operating a particulate matter sensor to produce raw data representing measurements of particulate matter in the air, evaluating pulses in the raw data to determine a pulse width and a maximum for each pulse, and identifying a type for the pollutant in the air using a classification model and data including the pulse widths and the maxima of the pulses. The data use in classification may further include non-particulate measurements from local chemical or environmental sensors and contextual data from the cloud or from local user devices.

23 Claims, 5 Drawing Sheets

(56) References Cited

U.S. PATENT DOCUMENTS

| | | | |
|---|---|---|---|
| 11,619,413 B2* | 4/2023 | Kwon | F24F 11/63 |
| | | | 700/276 |
| 2003/0051023 A1* | 3/2003 | Reichel | G01N 33/0075 |
| | | | 709/223 |
| 2011/0110558 A1* | 5/2011 | Branham | G01N 15/1433 |
| | | | 382/103 |
| 2017/0003221 A1* | 1/2017 | Takeda | G01N 15/1434 |
| 2017/0336313 A1* | 11/2017 | Iglseder | G01N 15/0205 |
| 2018/0246027 A1* | 8/2018 | Vacca | G01N 15/1434 |
| 2018/0259440 A1* | 9/2018 | Otsuka | G01N 15/14 |
| 2018/0266938 A1* | 9/2018 | Chow | H10F 39/803 |
| 2019/0285531 A1* | 9/2019 | Cooper | G08B 29/183 |
| 2020/0011779 A1* | 1/2020 | Lavrovsky | G01N 15/06 |
| 2020/0025665 A1* | 1/2020 | Trainer | G01N 21/53 |
| 2020/0378940 A1* | 12/2020 | Pariseau | G01N 33/0075 |
| 2021/0018210 A1* | 1/2021 | Nasis | F24F 11/65 |
| 2021/0164907 A1* | 6/2021 | Rode | G06N 3/04 |
| 2022/0205966 A1* | 6/2022 | Althoff | G01N 21/33 |

* cited by examiner

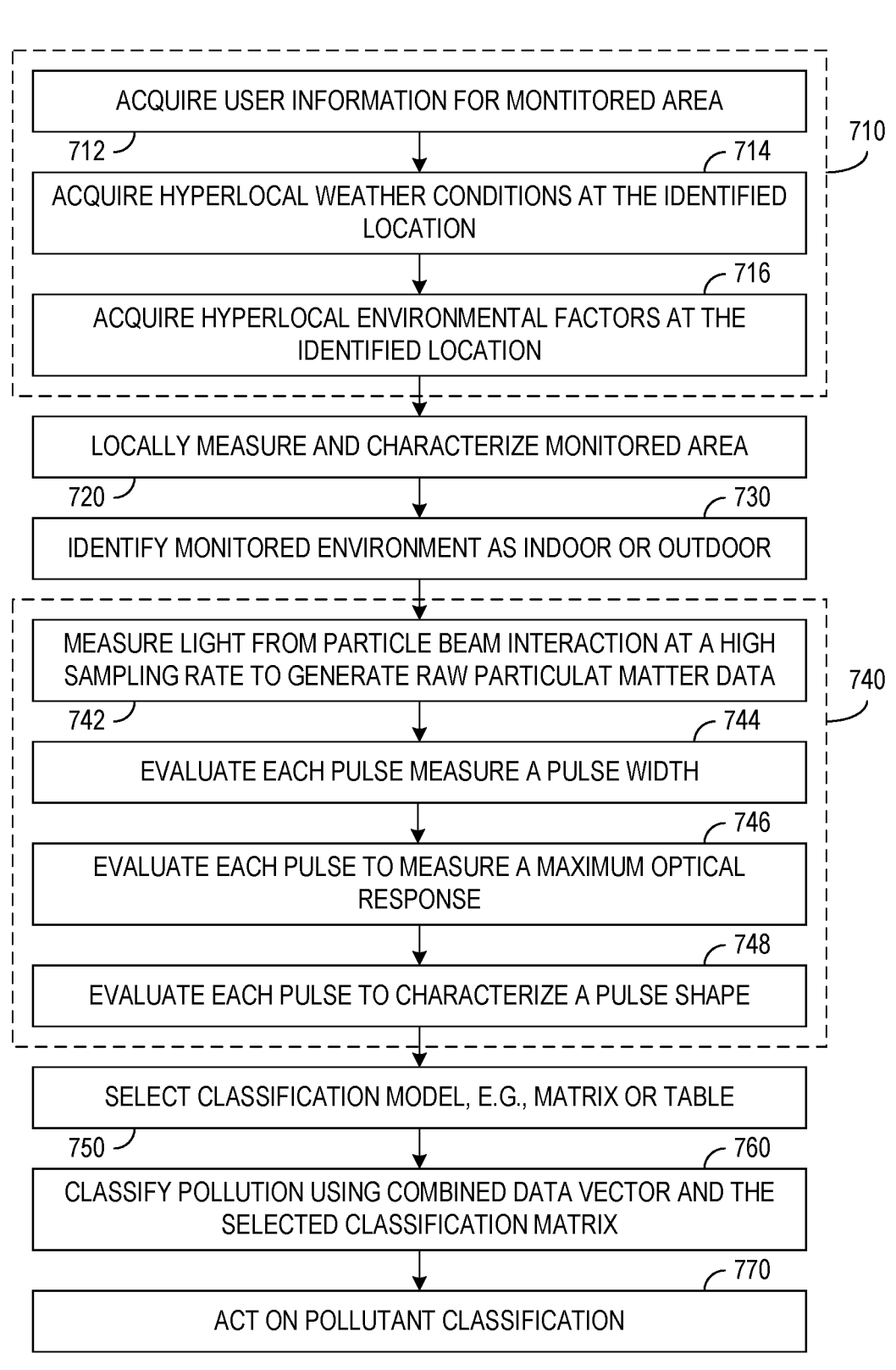

700

ACQUIRE USER INFORMATION FOR MONTITORED AREA
712

ACQUIRE HYPERLOCAL WEATHER CONDITIONS AT THE IDENTIFIED LOCATION
714

ACQUIRE HYPERLOCAL ENVIRONMENTAL FACTORS AT THE IDENTIFIED LOCATION
716

710

LOCALLY MEASURE AND CHARACTERIZE MONITORED AREA
720

IDENTIFY MONITORED ENVIRONMENT AS INDOOR OR OUTDOOR
730

MEASURE LIGHT FROM PARTICLE BEAM INTERACTION AT A HIGH SAMPLING RATE TO GENERATE RAW PARTICULAT MATTER DATA
742

EVALUATE EACH PULSE MEASURE A PULSE WIDTH
744

EVALUATE EACH PULSE TO MEASURE A MAXIMUM OPTICAL RESPONSE
746

EVALUATE EACH PULSE TO CHARACTERIZE A PULSE SHAPE
748

740

SELECT CLASSIFICATION MODEL, E.G., MATRIX OR TABLE
750

CLASSIFY POLLUTION USING COMBINED DATA VECTOR AND THE SELECTED CLASSIFICATION MATRIX
760

ACT ON POLLUTANT CLASSIFICATION
770

*FIG. 7*

POLLUTION TYPE SENSING

CROSS-REFERENCE TO RELATED APPLICATIONS

This patent document claims benefit of the earlier filing date of U.S. provisional Pat. App. No. 63/113,218, filed Nov. 13, 2020, which is hereby incorporated by reference in its entirety.

BACKGROUND

Air quality sensors are becoming more affordable and increasingly used by consumers and enterprises. Current air sensors include chemical sensors such as Volatile Organic Compound (VOC) sensors, Nitrous Dioxide ($NO_2$) sensors, environmental sensors such as humidity or temperature sensors, and particulate sensors (PM1.0, PM2.5, PM10). In many cases, current air quality sensors only measure pollutant metrics in general. For example, current particle sensors only measure the density or count of dust of a certain size (e.g., a PM2.5 sensor measures the concentration of dust that is 2.5 microns or less in diameter). Current particle sensors do not however, provide any specificity identifying a particle pollutant type (e.g., pollen, pet dander, mold spores, smog, etc.)

SUMMARY

In accordance with an aspect of the present disclosure, a pollution sensing system identifies a pollutant type using local sensor data and data from remote sources, e.g., cloud data. The sensor system generally includes a particle sensor and may include one or more local non-particulate sensors, e.g., chemical or environmental sensors, at the location being monitored. The local sensors provide the local measurement data. The sensor system may further acquire the remotely sourced data from IOT-enabled devices and the Internet. The remotely sourced data may be specific to the geolocation, time, or seasonality of the monitored area and may indicate environmental conditions such as air quality, prevalence of contagions such as flu viruses, prevalence of sources of allergens, mold, or pollen, and other available information concerning the monitored area and surroundings of the monitored area.

The pollution sensing system may perform a multifactor analysis of a combination of the locally measured data and the remotely sourced data to generate more specific classifications of measured pollutants. The multifactor analysis may use processes such as machine learning, regressions calculations, and other means to generate classification models or tables of pollutants. For example, an AI or machine learning process may identify and distinguish data patterns that correspond to different classifications or types of pollutants, and the pollution sensing system may provide a measurement of pollutant levels and an identification of the type or types of pollutants identified.

Current air quality sensor systems generally cannot identify or distinguish types of particulate pollutants and do not actively combine data from hardware environmental sensors with remotely sourced contextual data from the Internet (or user devices) in real-time to identify the pollutants encountered in a local environment. Sensing systems and methods as disclosed herein may use all data available from remote sources, nearby mobile devices, or the Internet, and from local sensors to identify the specific type(s) and/or origin(s) of measured pollutants.

A pollution sensing system or method as disclosed herein may report the classification of pollutants to a user through a user interface of the sensing system or through local devices. The sensing system may particularly generate warnings when an identified pollutant has a measured presence above a specific warning level. The pollutant classification may further be leveraged using network connected air treatment devices that may be automatically instructed to take the appropriate response to remove, reduce, or remedy the identified pollutant. For example, an Internet-enabled air treatment devices may respond according to the type, origin, or levels of detected pollution to improve air in the local environment.

BRIEF DESCRIPTION OF THE DRAWINGS

FIG. 7 is a flow diagram of a pollution sensing process in accordance with an example of the present disclosure.

The drawings illustrate examples for the purpose of explanation and are not of the invention itself. Use of the same reference symbols in different figures indicates similar or identical items.

DETAILED DESCRIPTION

Pollution sensing systems and methods as disclosed herein may use a multifactor analysis to identify pollutant types from measurements that local sensors in a monitored area produce and from context data that may be downloaded from the Cloud or from nearby devices. (Pollutant type as used herein refers to the source, structure, or nature of a particulate pollutant and not merely to the particle size for the pollutant, although the particle sizes, as described further below, may provide indicators for identifying a pollutant type.) The local measurements generally include measurement of particulate matter suspended in air in the monitored area and one or more other measurements of other properties of the monitored area. The multifactor analysis may employ tables or models that Artificial Intelligence (AI) or machine learning processes produce to characterize specific types of pollutants based on data patterns of local measurements and contextual data. Locally measured particulate data may include high-sample-rate measurements of light, e.g., intensity measurements, from particle interactions with a narrow or focused light beam. The intensity of interaction light at a series of times, from droplets in an aerosol or dust suspended in air may particularly be measured. Time variation in multiple measurements for a single particle, which may be represented as a pulse in the sampled measurements, may provide information regarding a characteristic, e.g., the size, shape, albedo, optical response, and composition, of that particle, and accumulated distributions of the characteristics of particles measured in an air sample during a time interval may provide further information regarding the type of pollutants present in the monitored area. Context data may indicate information about possible sources of suspended particles around the monitored area and information regarding other properties of local or hyperlocal surroundings around the monitored area. Context data may identify, for example, nearby sources of pollen and other dust, seasonal or weather information, the nature of nearby commercial facilities, or news regarding the occurrences of events such as nearby accidents or fires. Contextual data may further indicate features of the monitored area such as building information, including states of infrastructure like vacuum, air treatment, or HVAC systems, the age of building, which floor of the building is being monitored, or recent maintenance history for the building or other structure containing the monitored area.

Figure 1:
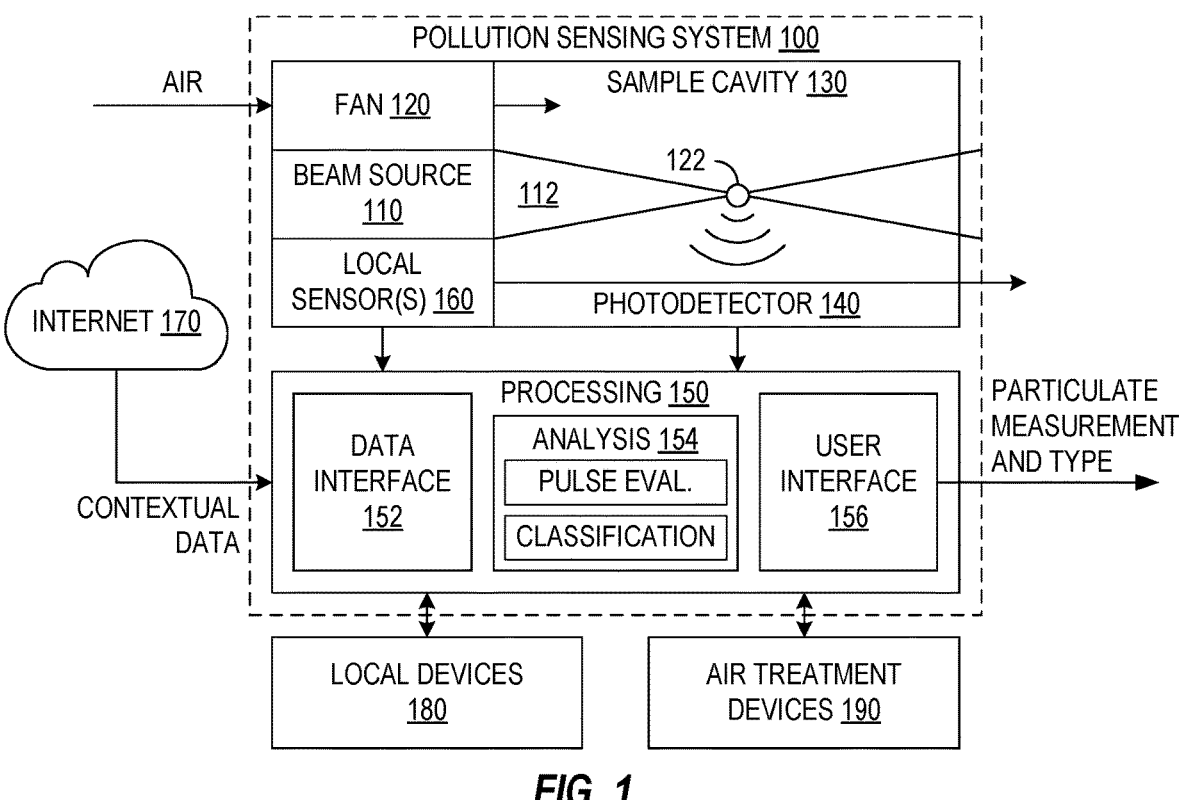
FIG. 1 is a block diagram of a pollutions sensing system in accordance with an example of the present disclosure.

FIG. 1 is a block diagram illustrating a pollution sensing system 100 in accordance with an example of the present disclosure. For particle measurements, system 100 of FIG. 1 includes a beam source 110, a fan or other air movement system 120, a sample cavity 130, and a photodetector 140. Beam source 110 may include a laser or other light source with an optical system that focuses a beam 112 into a localized sensing volume within sample cavity 130. The focus or size of beam 112 in the sensing volume may be such that only one particle at a time from an air sample is expected to enter the sensing volume and interact with beam 112. In one example, beam source 110 includes a laser, e.g., a laser diode producing UV or visible light, and beam 112 may be nearly monochromatic light having a wavelength between about 1,000 nm and 100 nm. Alternatively, beam source 110 may include one or more light emitting diodes (LEDs) or other light sources with a suitable optical system. In general, using shorter light wavelengths enables measuring smaller particles.

Fan 120 draws air from the monitored area and directs the drawn air (including suspended particulates) into and through sample cavity 130, so that individual particles 122 cross through the sensing volume inside sample cavity 130. Fan 120 may operate continuously so that the air sample in sample cavity 130 is constantly being replenished from the monitored area. Each particle 122 passing through the sensing volume interacts with focused beam 112, e.g., reflects, refracts, scatters, or absorbs light from beam 112. Photodetector 140 is adjacent to the sensing volume in sample cavity 130 and positioned to receive light from the interaction of each particle 122 with beam 112. In particular, while a particle 122 from the sampled air passes through the sensing volume where beam 112 is focused, the particulate 122 reflects or scatters UV light onto photodetector 140.

Figure 2:
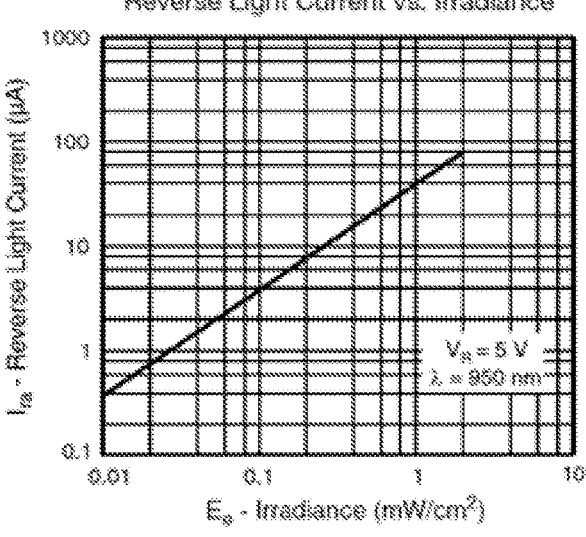
FIG. 2 illustrates the voltage response of a photodiode as a function of incident irradiance.

Photodetector 140 reacts to incident light to produce an electrical response. Photodetector 140, for example, may include one or more photodiodes. Irradiance incident on a photodiode causes a well-known reaction causing the photodiode to produce an analog electrical signal. FIG. 2, for example, shows a log-log plot of how a reverse current $I_{RA}$ that an example diode generates depends on an irradiance $E_o$ incident on the photodiode. In general, photodetector 140 may produce an electrical current or voltage response that depends on the irradiance or intensity and wavelength of the light incident on a sensing area of photodetector 140. The response of different photodetectors 140, e.g., in different examples of sensing system 100, may be calibrated or corrected to provide a standardized response that allows comparisons and matching of outputs from different photodetectors 140.

Figure 3:
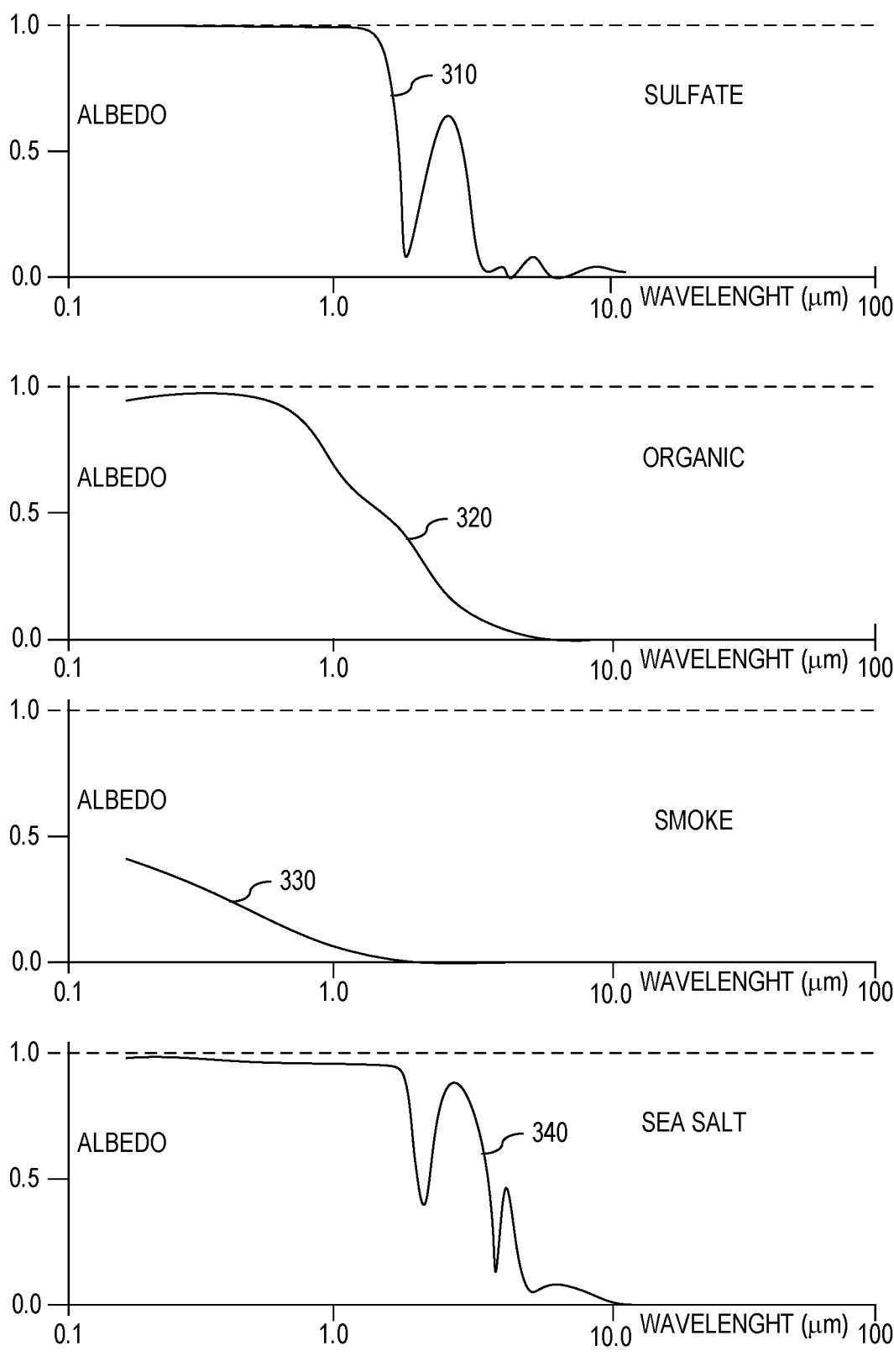
FIG. 3 illustrates the different dependences that reflected or scattered irradiances from different types of particulates have on incident light wavelength.

The capability of photodetector 140 to accurately sense particles through light dispersion can be affected by several issues, including the color and surface texture of the particle. White particles, for example, generally scatter more light than darker particles, so that counting or detecting particles based solely on measured light intensity can lead to falsely higher or lower readings since detection may be more sensitive to reflective particles. FIG. 3 contains examples of plots 310, 320, 330, and 340 showing how the albedos or optical reactions of different types of particulates, e.g., sulfate, organic, smoke, and sea salt particles, vary as functions of incident light wavelength. For any wavelength of light beam 112 in system 100 of FIG. 1, different particle types of the same size can produce different optical responses. Different cities and other regions often have different air pollutants with different structures and colors, and the difference between the pollution in different regions can make measurements of particulate pollutants more difficult or inaccurate.

A processing system 150 in pollution sensing system 100 of FIG. 1 is connected to photodetector 140. Processing system 150 may include a conventional microprocessor or microcontroller with memory, input/output interfaces, and suitable software or firm to implement a data interface 152, an analysis module 152, and a user interface 145. Processing system 150 may acquire local particulate measurement data, local non-particulate measurement data, and contextual data through data interface 152. Analysis module 152 may analyze all available data for identification of pollution types in the monitored area, and examples of analysis processes are described further below. User interface 156 may incorporate hardware such as a display through which a user of sensing system 100 may be informed regarding the pollutants identified in the monitored area or may incorporate interfaces for communication with one or more local devices 180, e.g., mobile phones or computers, to convey warnings or information or to receive user instructions. As described below, user interface 156 may also communicate with one or more air treatment devices 190 to begin air treatment or other action that is appropriate to the type and level of pollution system 100 identified in the monitored area.

In accordance with an aspect of the present disclosure, data interface 152 may sample the electrical output from photodetector 140 at a high frequency, e.g., above 50 kHz or between about 100 and 500 kHz, to provide raw particulate measurement data to analysis module 154. With high-frequency sampling, each transit of a particle 122 through the sensing volume in sample cavity 130 provides multiple optical response measurements from photodetector 140. Typically, the optical response from the interaction of a particle 122 with beam 112 may be smaller when a leading edge of the particle 122 enters the sensing volume, larger when or while the maximum interaction of the particle 122 with light in the sensing volume occurs, and smaller again when only a trailing edge of the particle interacts with the sensing volume. The data associated with particulate measurements or samples of the electrical output from photodetector 140 typically displays pulses, and each pulse may correspond to individual particle 122 passing through the focus of beam 112. Analysis module 154 may evaluate the shapes of the pulses to determine information regarding characteristics, e.g., the size, shape, reflectivity, color, and type, of the particulate 122.

Data interface 152 and analysis module 154 of processing system 150 generate and analyze local particulate data from photodetector 140 and may further acquire and analyze local data from local sensors 160 or local devices 180. Local sensors 160 may measure one or more different properties or characteristics of the air sample in sample cavity 130 or measure one or more properties or characteristics of the monitored area. For example, local sensors 160 may measure temperature, humidity, or the presence of one or more specific chemicals in the air sample in sample cavity 130 or in the air around sensing system 100. Local devices 180, e.g., nearby smartphones or computer systems, may also contain sensors capable of local measures of the monitored area.

Processing system 150 receives and analyzes the local data, e.g., particulate data from photodetector 140 and other local measurement data from sensors 160 or local devices 180, and data interface 152 may also be configured to acquire contextual data from the cloud, e.g., the Internet 170 or from local devices 180. For example, data interface 152 may access one or more public or proprietary websites to download contextual data that is associated with the location of the monitored area and the current time. In some implementations, data interface 152 includes a Wi Fi enabled integrated circuit chip that is configured or used to connect to the Internet 170 or local devices 180 through a wireless network in the monitored area and to download contextual data to processing system 150. The contextual data may, for indicate the location or GPS coordinates of the monitored area or features, conditions, or events that may be near the monitored area or in a neighboring area surrounding the monitored area. For example, the monitored area may be an indoor area or a home or other building, and the contextual data may indicate characteristics of a neighborhood or region containing the home or other building, and the contextual data may identify flora, fauna, commercial or industrial facilities, or events such as fires in the neighborhood or region around the monitored area. Contextual data may identify likely or candidate particulates such pollen, pet dander, mold spores, traffic particles, industrial pollutants, smoke from a nearby fire that may be present in the neighborhood or region surrounding the monitored area. Such contextual data may be obtained from reliable sources, e.g., from government services such U.S. EPA air quality station data from the U.S. EPA website or weather data from the national weather service website, or from a proprietary source that may be associated with the manufacturer of sensing system 100. Analysis module 154 in processing system 150 may use all available data, e.g., local particulate and non-particulate measurements and contextual data to measure particles and identify particulate pollution types.

Figure 4:
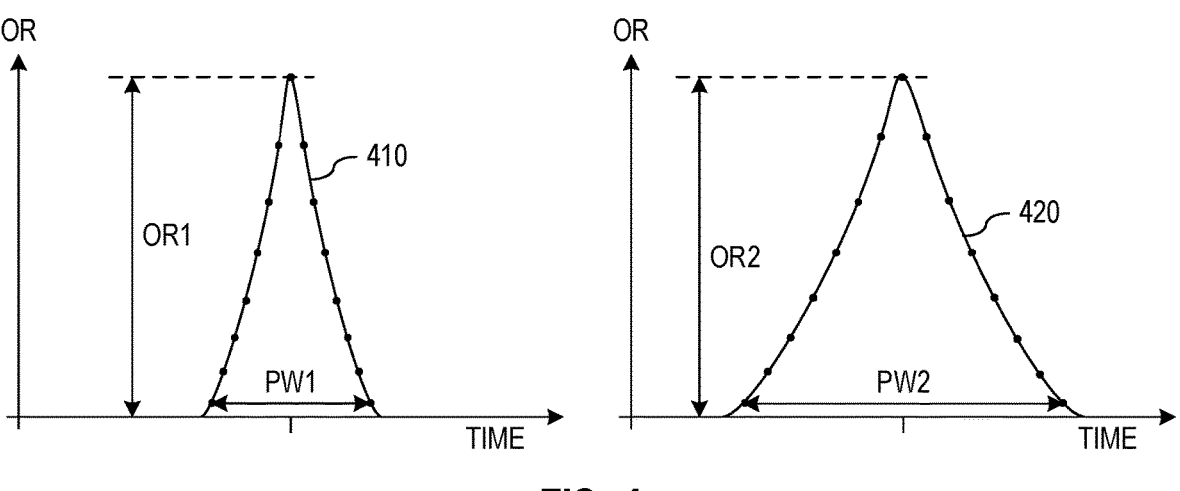
FIG. 4 illustrates pulses in photodetector output signal as particles of different sizes pass through a focused light beam.

In accordance with an aspect of the current disclosure, local particulate measurements use high-frequency (e.g., 50 kHz or more) sampling of optical response to detect individual particles as data pulses. Analysis module 154 of processing system 150 evaluates the pulses in measured light intensity from particle-beam interactions. FIG. 4 illustrates examples of pulses 410 and 420 in samples of a raw signal from photodetector 140 when particles of different sizes pass through the sensing volume in sample cavity 130. The width of each pulse indicates the time during which the particle 122 interacted with beam 112 in the sensing volume. Given a known air flow speed in cavity 130, which is dictated by the rotational speed of fan 120, the width PW1 or PW2 of each pulse 410 or 420 corresponds to the size of the detected particle, e.g., the diameter of a particle larger than the focused size of beam 112 depends on the product of the particle velocity and the interaction time. The measured width of each pulse 410 or 420 may be defined in-differently. A width may be the time associated with the full width at half maximum of the pulse or the time between when the measured irradiance rises above a background noise level and when the measured irradiance next falls to the background noise level. The width PW1 or PW2 of each pulse 410 or 420 is largely unaffected by the color, surface texture, or type of particulate and thus provides information about particle size that is largely independent of the particle type. The larger the particle, the longer the measured pulse width. In contrast, the height OR1 or OR2 of each pulse 410 or 420 in measured irradiance depends on optical response or the albedo of the associated particle 122 at the wavelength of incident beam 112 and thus provides information about the characteristics of the particle 122. For example, the maximum measured irradiance may indicate a product of the albedo of the particle and the cross-sectional area of the particle.

Figure 5:
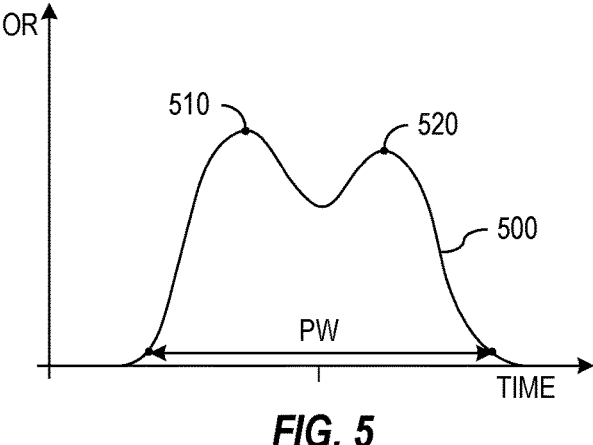
FIG. 5 illustrates the shape of a pulse in photodetector output signal as a particle with a complex surface or composition passes through a focused light beam.

The shape of a pulse in raw particulate data may also provide information regarding the type or composition of a particle. Pulses 410 and 420, for example, are symmetric about their maxima and have measured intensity that rise smoothly to the maxima and drop smoothly from the maxima. Such shapes for pulses 410 and 420 suggest particles with uniform and smooth surfaces, e.g., solid spherical particles. A pulse may instead have an irregular shape that suggests an irregular or complex particle shape or internal structure. FIG. 5 shows a curve 500 in irradiance samples having two peaks 510 and 520. A double-peak pulse as shown in FIG. 5 may indicate a particle with a complex shape or internal structure or two particles passing through the sensing volume at about the same time.

Figure 6:
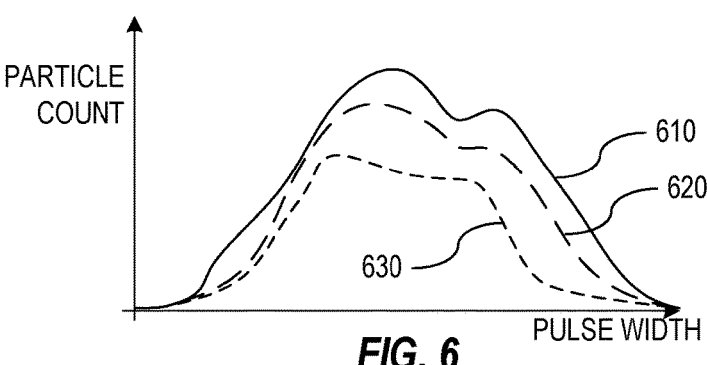
FIG. 6 illustrates how measurements of particulate matter may vary over time in a manner that is potentially useful in classifying a type of pollutant.

A pollutant may include particles with different characteristics, e.g., particles of different sizes, shape, or albedo. Accordingly, a measured distribution of number of particles in an air sample having each value of a characteristic may provide information to distinguish different pollutant types. FIG. 6, for example, illustrates an example where a distribution 610 represents the occurrences of particles measured to have a range of sizes. Distribution 610 may be a histogram of pulse width measurements during a time interval ΔT1. The average size and the shape of the distribution may be characteristic of different types of pollutants.

Analysis of distribution changes over time may also yield additional information about the type of particle or particles. For example, FIG. 6 shows distributions 610, 620, and 630 that air samples from the same monitored area may have at different times. For example, distributions 610, 620, and 630 may be histograms of diameter measurements during three sequential time intervals ΔT1, ΔT2, and ΔT3. Changes in the distribution may, for example, result from settlement of particles in the monitored area. The manner or way that a such a distribution changes may be characteristic of the type of pollutant, e.g., household dust tends to settle quickly compared with smoke or water vapor. The potential pollutant may be identified by reviewing the signal pattern over time, e.g., a settling pattern.

People may need or want to identify or distinguish which of a large number of possible air pollutants are in a monitored area. A sensor system may need to identify a specific pollutant from among various industrial pollution, various types of smoke, pollen, or pet dander. Hardware that is specific to each type of pollutant may be impractical. To improve the classification and prediction of the type of a measured pollutant, pollutions sensing system 100 of FIG. 1 uses processing system 150 with analysis module 154 to combine and analyze local particulate and non-particulate measurement data with contextual data and thereby identify or distinguish any desired number of different pollution types.

FIG. 7 illustrates an example process 700 that a sensing system such as sensing system 100 of FIG. 1 can employ to identify a pollution type in a monitored area. Process 700 employs multiple sources to provide multiple types of information and measurements. The information used generally includes contextual information that may affect the monitored area and local particulate and non-particulate measurements of the monitored area. A block 710 of process 700 acquires contextual information for identification of pollution type. Block 712 represents acquisition of user information for the monitored area. User information may include the current time, the location or coordinates of the monitored area, and user background information, e.g., information regarding pets in the house or other monitored area and the age and type of building being monitored. A sensing system may acquire such user information through a user interface of the sensing system, e.g., user interface 156 in FIG. 1, or through a user device, e.g., local device 180 in FIG. 1. In particular, a user of sensing system 100 may begin operation of sensing system 100 by responding to questions presented to the user through user interface 156 or through an app running on a local device 180. With the location for the monitored area known, the sensing system in blocks 714 and 716 can access the cloud to acquire weather conditions, e.g., hyperlocal weather data that may be specific and applicable to a street and block containing the monitored area, and other data identifying any other relevant environmental factors that may affect the location of the monitored area. The other relevant information that process block 716 may acquire from the cloud or Internet includes, for example, a current air quality index (AQI), a pollen count, a pollen type currently in the surroundings, traffic data, news of major events (e.g., forest fires), and other information regarding events or fixtures that may be close enough to affect the monitored area. Such information may be acquired from government, third-party, and crowd-sourced data sources.

Hyperlocal environmental information for contextual data may be predicted or derived by using weather and aerosol or pollutant dispersion models alongside trusted data, e.g., from government weather stations. For example, weather and aerosol dispersion models can be used with information from trusted stations to predict hyperlocal environmental data that applies to surroundings at a scale of one or a few city blocks. By using regression and machine learning models of government environmental station data versus the geographic surroundings (trained by crowdsourced sensors and other government stations), the sensing system or a cloud source of contextual information can accurately predict the pollution level at potentially any location near a government station.

A process block 720 of process 700 acquires one or more non-particulate measurements of the monitored area or of an air sample currently being analyzed. For example, local sensors 160 in sensing system 100 of FIG. 1 may include a temperature sensor, a humidity sensor (e.g., a hygrometer), a microphone, an ambient light sensor, or a chemical sensor such as a total volatile organic compound (TVOC) sensor, a carbon dioxide ($CO_2$) sensor, a carbon monoxide (CO) sensor, or a sensor for oxides of nitrogen ($NO_x$) that can measure the monitored area.

The local non-particle measurements will normally be the same as or very similar to corresponding contextual data if the monitored area is outdoors. A process block 730 compares local sensor environmental measurements from process block 720 with corresponding reported public data from process block 714 to determine whether the monitored area is indoors or outdoors, which may be important in the classification of a pollutant. For instance, temperature or humidity measurements from local sensors or devices that vastly differ from weather reports from the Internet can suggest that the local sensors are not outdoors. However, similar temperature and humidity might indicate that the external data may correspond more to the monitored area. Table 1 shows local environmental sensor data that can be compared with outdoor environmental and weather data to determine whether a sensing system is indoors or outdoors.

TABLE 1

| Distinguishing Indoor from Outdoor Environments | |
| --- | --- |
| Sensors | Insight |
| Temperature | Is the sensor different than the outside data? |
| RH | Is the sensor different than the outside data? |
| Noise | What does the noise profile indicate? |

A process block 740 of process 700 measures suspended particulate matter in the sampled air. As described above, process block 740 may include a process block 742 that measures light from beam-particle interactions at a high sampling rate to generate raw particulate matter data. The raw particulate matter data is generally made up of datum, each indicating an optical response at a time corresponding to the datum, and collectively represent pulses that occur when particles in the interaction volume interact with the beam. A process block 744 evaluates each pulse in the particulate matter data to measure a pulse width for the pulse. As noted above, the pulse width may be an indication of the size of a particle. A process block 746 evaluates each pulse in the particulate matter data to measure a maximum pulse height for the pulse. As noted above, the maximum pulse width may indicate a maximum optical response, which may be an indication of an albedo of the particle for the wavelength of the incident light. A process block 744 evaluates each pulse in the particulate matter data to characterize a shape of the pulse. As noted above, the character of the pulse shape may be an indication of surface features or composition of a corresponding particle.

Figure 8:
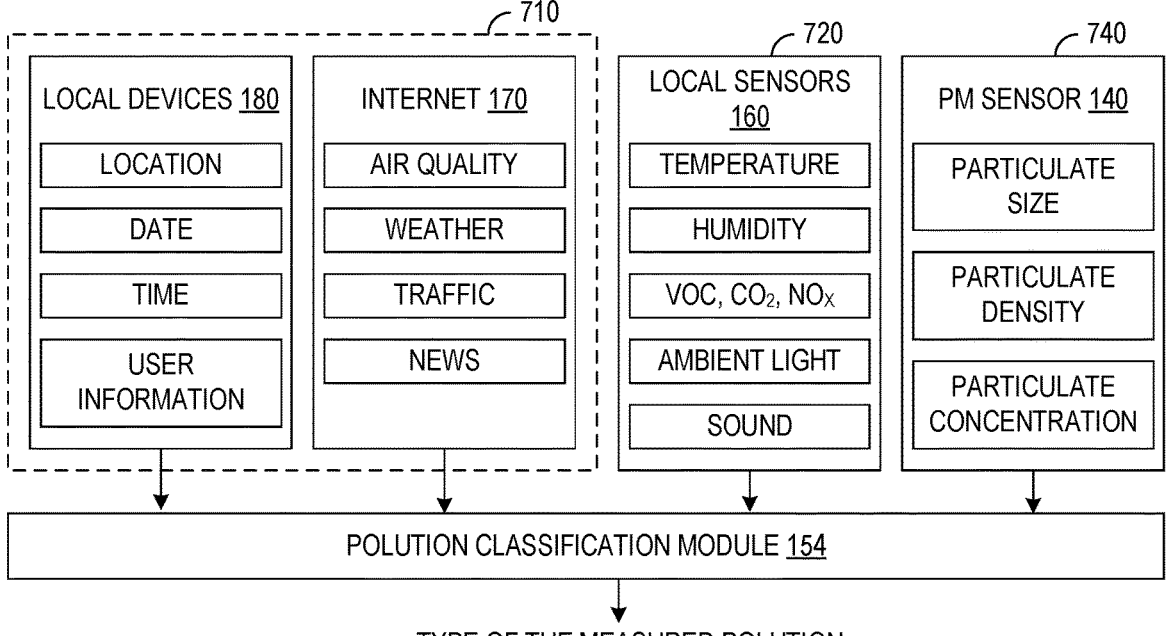
FIG. 8 illustrates an example of multiple sources providing a data set to a pollution classification module that classifies pollution present in a monitored area.

Process blocks 710 to 740 provide a data set that a processing system can analyzed to identify a type of pollutant that is being measured. As described above, the information corresponds to factors used in a multifactor determination or classification of pollution type. FIG. 8 illustrates potential sources of data that a pollution classification or identification process can combine. In particular, for contextual data of process block 710, local devices 180 of FIG. 1 can provide location, data, time, and user information for the monitored area, and the Internet 170 can provide air quality, weather, traffic, and news information affecting the monitored area. Local sensors 160 can provide measurements of temperature, humidity, carbon dioxide ($CO_2$) concentration, carbon monoxide (CO) concentration, oxides of nitrogen ($NO_x$) concentrations, volatile organic compound (VOC) concentration, and noise and ambient light levels in the monitored area. PM sensor systems, e.g., photodetector 740, provides raw measurements of particles. All the information from these sources may input to a classification portion of analysis module 154, and the pollution classification portion may employ machine learning, expert models, and other analysis techniques in determining the potential type of pollutant encountered.

Returning to FIG. 7, a process block 750 of process 700 selects a classification model, matrix, or table for the analysis of the multifactor information. The classification model, matrix, or table may depend on the types of pollution that may be expected in the monitored area or the types of pollution of particular concern to the user. For example, the contextual data may be used to select a classification table or matrix covering a target set of pollutant types. Alternatively, a classification matrix or table may cover as large of a set of pollutant types as possible.

A process block 760 uses the selected classification table or matrix and a data vector including local particulate data, local non-particulate data, and contextual data to classify a pollutant in the monitored area. Table 2 shows an example of a pollution classification matrix that uses factors including local particulate data, local gas data, and contextual Internet data to distinguish among a set of different pollutant types. Table 2 may be generated based on statistical measurements of the listed data factors in samples known to contain the identified pollutants. In Table 2, particulate data factors include an average particulate size and an average particulate optical response. Local gas data include volatile organic compound (VOC) level and relative humidity (RH) as locally measured. Contextual Internet data classification factors include pollen data, maps and data concerning airborne contagions such as flu viruses, the air quality index (AQI) for the neighborhood around the monitored area, and weather factors such as relative humidity.

region around the monitored area displayed high levels of oak pollen (from a third-party source such as pollen.com), then the pollution sensing system can report the potential for oak pollen in the monitored area.

Figure 9:
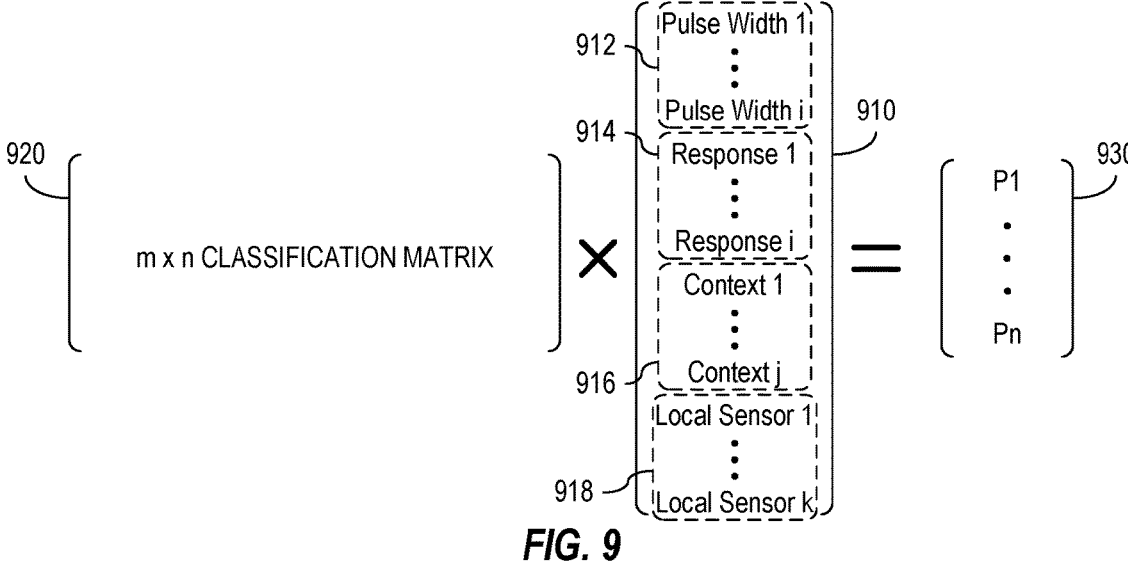
FIG. 9 illustrates an example of a process that identifies a type for pollution using a data vector including particulate matter measurements, local non-particulate measurements, and contextual data and a classification matrix that machine learning or statistical processes may generate.

FIG. 9 illustrates an alternative process for classifying pollutants in an air sample, which may be used in process block 760 of FIG. 7. Using the technique of FIG. 9, the multifactor data set is organized as a data vector 910. Data vector 910 has an integer number m of components, where the number m defined by a syntax for data vector and the syntax defines what each component of data vector 910 represents. The components of data vector 910 include particulate measurements 912 and 914, contextual data 916, and local sensor data 918. The particulate measurements in this example correspond to measurements 912 of the pulse width and measurements 916 of the maximum optical response for each of a number i of pulses. (The number i may be a fixed integer, e.g., about 0 to 5,000, depending on sample speed, pollutant concentration, and the length of sensing time.) Each pulse width or optical response measurement 912 or 914 may be represented using a multi-bit component, e.g., 6-bit to 8-bit value, that allows 64 to 256 distinct measurement values for pulse width and optical response. An alternative way to format particle measurements 912 and 914 is as representations of distributions of particle measurements. For a particle width distribution, each component of pulse width measurements 912 may indicate a count of detected particles having a measured width in a range or bucket corresponding to the component, and the number i of components or buckets in the distribution may be around 50 or more, e.g., 64 pulse width buckets. Optical response data 914 may similarly represent a distribution or histogram of the optical response measured from pulses in the raw data. Data vector 910 further includes a number j of contextual values 916. The contextual compo-

TABLE 2

| Pollutant | Particulate | | Gas | | Contextual Internet Data | | | | |
|---|---|---|---|---|---|---|---|---|---|
| | Size | Optical Response | VOC | RH | Pollen Data | Flu Map | AQI Data | Flu Data | Flu RH |
| Cooking Smoke | Medium | Small | High | High | N/A | N/A | N/A | N/A | Low |
| Smoking | Small | Small | High | N/A | N/A | N/A | N/A | N/A | N/A |
| Dust | Small | Small | None | N/A | N/A | N/A | N/A | N/A | N/A |
| Pet/Human Dander | Large | Medium | None | N/A | N/A | N/A | N/A | N/A | N/A |
| Off-Gassing | None | None | High | N/A | N/A | N/A | N/A | N/A | N/A |
| Oak Pollen | Large | Large | None | N/A | High | N/A | N/A | N/A | N/A |
| Outside Air Pollution | Small | Small | None | N/A | N/A | N/A | High | N/A | N/A |
| Sneezing Aerosol | High | Low | Low | Med | N/A | High | N/A | High | N/A |
| Stuffy/High CO₂ | None | None | High | Med | N/A | N/A | N/A | N/A | N/A |

The data vector combines hardware data from sensors like the PM sensor, which yields size and optical response distributions, local measurements other sensors, and cloud information. Process block 760 may classify the pollutant by identifying which row of the classification matrix most-closely matches the data vector to determine the classification or type of pollutant. If, for example, larger particles corresponding to oak pollen were seen in the size distribution from the particulate data, and contextually it was pollen season, the user was outside, the weather was conducive to pollen being dispersed in the air, and the specific location nents 916 may be numeric or Boolean values that identify any of the contextual information discussed above. Similarly, the local sensor components 918 may be numeric or Boolean values that represent measurements taken of the monitored area or the air sample.

Data vector 910 is multiplied by a m-by-n classification matrix 920 to produce an n-component result vector 930. For this method, processing system 150 of pollution sensing system 100 shown in FIG. 1 may contain a processor implementing matrix multiplication processes. The number n may be the number of candidate pollution types, and each of the components P1 to Pn of result vector 930 is proportional to a probability that the data vector 910 corresponds to measurements of a pollutant type corresponding to that component of vector 930. In most cases, the identified classification of the pollutant is the pollutant corresponding to the component P1 to Pn having the largest value.

Each row of matrix 920 corresponds to a data pattern for a corresponding pollutant type. Matrix 920 may be generated at a factory or laboratory or even in the user environment using machine learning or statistical methods. For example, a software app (in the user interface of the sensing system or in a device capable of communicating with the sensing system) can ask a user whether the user experienced a specific pollen allergy when the sensor detected the presence of a specific allergen (e.g., oak pollen). If the prediction is determined to be correct by the user, the learning strengthens the potential of the classification matrix 920 to predict such as result in the future for other users in similar situations. By recording the types and classifications of pollutants encountered by geography and season (January vs. June for example), improvements can also be made on the calibration of any pollution sensing system. This data, e.g., the classification matrix, can be sent to a pollution sensing system at the time of manufacturing and in real time via updates through available networks, e.g., the Internet. For example, if the pollution sensing system is known to be used in London it may need a different calibration method than if the pollution sensing system were used in India.

Process 700 of FIG. 7 may further employ a process block 770 to act on the pollution classification found. Depending on the pollutant or environmental issue detected, an automated and appropriate response may be generated to ameliorate the pollutant or issue. For example, if block 760 identified cooking smoke the pollution sensing system may provide a warning to the user or may recommend an oil with a higher temperature smoke point. If an air treatment device is available, the pollution sensing system executing process block 770 may transmit instructions to the air treatment device or other environmental system, e.g., a robotic vacuum or an HVAC system, to begin removing the classified pollutant from the monitored area. If the pollutant is a product of human activity, the pollution sensing system executing process block 770 may provide information or recommendations concerning the activity. The recommendations can be sent via a mobile app with wireless connectivity (e.g., cellular/Wi-Fi/Bluetooth) and proactive actions may be taken by the user or internet-enabled devices. Table 3 provides further examples of actions that a pollution sensing system may take in response classifying a pollutant in a monitored area.

TABLE 3

| Action Taken in Response to Classification of Pollutants | |
| --- | --- |
| Pollutant | Action |
| Cooking Smoke | Recommend better oil |
| Tobacco Smoke | Health Notice |
| Dust | Automatically Vacuum Floor |
| Pet/Human Dander | Automatically Vacuum Floor |
| Off-Gassing | Turn on Air-Exchanger/Open Window |
| Pollen | Close Window/Turn on Purifier/Recommend Medicine |
| Outside Air Pollution | Close Window/Turn on Purifier |
| Sneezing aerosol | Turn up Heat/Suggest Medicine |
| Stuffy/High CO2 | Turn on Air-Exchanagr/Open Window |

12

Each of modules disclosed herein may include, for example, hardware devices including electronic circuitry for implementing the functionality described herein. In addition or as an alternative, each module may be partly or fully implemented by a processor executing instructions encoded on a machine-readable storage medium.

All or portions of some of the above-described systems and methods can be implemented in a computer-readable media, e.g., a non-transient media, such as an optical or magnetic disk, a memory card, or other solid state storage containing instructions that a computing device can execute to perform specific processes that are described herein. Such media may further be or be in a server or other device connected to a network such as the Internet that provides for the downloading of data and executable instructions.

Although particular implementations have been disclosed, these implementations are only examples and should not be taken as limitations. Various adaptations and combinations of features of the implementations disclosed are within the scope of the following claims.

What is claimed is:

1. A process for identifying a pollutant in air at a monitored area, the process comprising:

operating a particulate matter sensor to produce raw data representing measurements of particulate matter in the air at the monitored area, wherein the raw data includes samples of measured light intensity from particle-beam interactions; and identifying a type of the pollutant in the air through a classification process that analyzes a data set constructed using the raw data, wherein the classification process includes:

evaluating a plurality of pulses in the raw data to determine pulse widths, pulse heights, and pulse shapes for the plurality of pulses, each pulse of the plurality of pulses including multiple samples for at least one particle and particle-beam interaction for the at least one particle, a pulse width of each pulse corresponding to a size of the at least one particle and a speed of the at least one particle, a pulse height of each pulse corresponding to albedo of the at least one particle and a cross-sectional area of the at least one particle;

including, in the data set, components derived from the pulse widths, the pulse heights, and the pulse shapes of the plurality of pulses; and identifying the type of the pollutant using the components derived from the pulse widths, the pulse heights, and the pulse shapes of the plurality of pulses by:

constructing a data vector from the data set, wherein the data vector includes local particulate data, local non-particulate data, and contextual data, and the local particulate data includes size and optical response distributions based on the pulse widths and the pulse heights of the plurality of pulses;

multiplying the data vector and a classification matrix, wherein the classification matrix is generated through a machine learning process trained using a plurality of air samples respectively containing a plurality of different types of pollutants, and the classification matrix encodes data regarding local particulate data, local gas data, and contextual Internet data for the plurality of different types of pollutants; and classifying the pollutant based on a result of the multiplying of the data vector and the classification matrix.

2. The process of claim 1, further comprising operating a chemical sensor to measure a chemical in the air at the monitored area, wherein the data set includes one or more components based on one or more measurements of the chemical from the chemical sensor.

3. The process of claim 2, wherein the chemical is one of a volatile organic compound (VOC), carbon dioxide ($CO_2$), carbon monoxide (CO), and an oxide of nitrogen ($NO_x$).

4. The process of claim 1, further comprising operating an environmental sensor to measure an environmental characteristic of the monitored area, wherein the data set includes one or more components based on one or more measurements of the environmental characteristic from the environmental sensor.

5. The process of claim 4, wherein the environmental characteristic is one of noise, humidity, temperature, and light in the monitored area.

6. The process of claim 4, further comprising obtaining environmental information applicable to surroundings of the monitored area, wherein the classification process further includes comparing the environmental characteristic measured by the environmental sensor to the environmental information and determining whether the monitored area is indoors or outdoors based on a comparison result between environmental characteristic and the environmental information.

7. The process of claim 1, further comprising obtaining contextual data applicable to the monitored area, wherein the data set further includes one or more components based on the contextual data.

8. The process of claim 7, wherein the contextual data identifies one or more of a location, a time, a season, current weather, public air quality information, allergen information, disease information, news, building information, infrastructure information, an age of a building, a floor, and recent maintenance that applies to surroundings of the monitored area.

9. The process of claim 7, wherein the contextual data represents hyperlocal information that is specific to a street or block on which the monitored area is located.

10. The process of claim 1, further comprising obtaining further information from a local device in the monitored area, wherein the data set includes one or more components based on the further information.

11. The process of claim 10, wherein the local device comprises one of a mobile device, a computer, or a network device.

12. The process of claim 10, wherein the further information from the local device comprises user information to identify characteristics of the monitored area.

13. The process of claim 1, wherein operating the particulate matter sensor comprises:

directing a light beam into a portion of the air at the monitored area; and sampling an output signal from a photodetector that is positioned to measure light produced from interactions of particles with the light beam, wherein the sampling is at a frequency that produces the multiple samples.

14. The process of claim 13, wherein the sampling is at a frequency above 50 KHz.

15. The process of claim 1, wherein the classification process includes determining a pattern of change over time in the raw data, the pattern of change being a factor that the classification process uses to distinguish different types of pollutants.

16. The process of claim 1, further comprising responding to identification of the type of the pollutant by performing one or both of:

generating a warning alert specifying the type of the pollutant; and activating an air treatment system.

17. The process of claim 1, wherein the classification process selects the type of the pollutant from a set of pollution types including aerosols, smoke, cigarette smoke, vape smoke, fire smoke, pollen, dander, mold spores, and smog.

18. A pollution sensing system comprising:

a beam source positioned to direct a beam into an air sample from a monitored area;

a photodetector positioned to sense light produced by interactions of the beam with particulate matter in the air sample; and a processing system connected to the photodetector, the processing system implementing:

a data interface configured to produce raw data by sampling an output signal from the photodetector, wherein the raw data includes samples of measured light intensity from particle-beam interactions;

a pulse evaluation module configured to:

identify, in the raw data, pulses corresponding to a plurality of particles of the particulate matter, wherein each pulse of the pulses includes multiple samples for at least one particle and particle-beam interaction for the at least one particle; and, for each pulse, determine a characteristic of a particle corresponding to a pulse, wherein the characteristic corresponds to a size and/or albedo of the at least one particle based on width and/or height of the pulse; and a classification module configured to identify a type of a pollutant in the air sample through a classification process that analyzes data representing a distribution for characteristics of the plurality of particles, wherein the classification process includes:

constructing a data vector from the raw data and distribution for the characteristics, wherein the data vector includes local particulate data, local non-particulate data, and contextual data, and the local particulate data includes distributions the size and the albedo based on pulse widths and pulse heights of a plurality of pulses;

multiplying the data vector and a classification matrix, wherein the classification matrix is generated through a machine learning process trained using a plurality of air samples respectively containing a plurality of different types of pollutants, and the classification matrix encodes data regarding local particulate data, local gas data, and contextual Internet data for the plurality of different types of pollutants; and classifying the pollutant based on a result of the multiplying of the data vector and the classification matrix.

19. The pollution sensing system of claim 18, further comprising one or more chemical sensors that measure chemicals in the air sample at the monitored area, wherein the data that the classification module uses further includes one or more measurements of the chemicals from the one or more chemical sensors.

20. The pollution sensing system of claim 18, further comprising one or more environmental sensors that measure one or more environmental characteristics of the monitored area, wherein the data that the classification module uses further includes one or more measurements from the one or more environmental sensors.

21. The pollution sensing system of claim 18, wherein the data interface is further configured to contextual data applicable to the monitored area, wherein the data that the classification module uses further includes the contextual data.

22. The pollution sensing system of claim 18, wherein the classification module identifies the type for the pollutant to be one of an aerosol, smoke, cigarette smoke, vape smoke, fire smoke, pollen, dander, mold spore, and smog.

23. A process for identifying a pollutant in a monitored area, the process comprising:

passing air from the monitored area through a sample cavity;

directing a light beam into the sample cavity;

sampling, as a plurality of samples, an output signal from a photodetector that is positioned to measure light produced from interactions of the light beam with particulate matter in the air passing through the sample cavity, wherein the sampling is at a frequency that produces multiple samples for each particle in a plurality of particles of the particulate matter;

identifying, in the plurality of samples, a plurality of pulses, the plurality of pulses respectively corresponding to the plurality of particles;

for each of the plurality of pulses, using a set of samples corresponding to a particle and a pulse to determine a characteristic of the particle, wherein the characteristic corresponds to a size and/or albedo of the particle based on width and/or height of the pulse;

including, in a data set, a representation of a distribution of the characteristics of the plurality of particles; and identifying a type of the pollutant in the air through a classification process that analyzes the data set, wherein the classification process includes:

constructing a data vector from the data set and the distribution for the characteristics, wherein the data vector includes local particulate data, local non-particulate data, and contextual data, and the local particulate data includes distributions of the size and the albedo based on pulse widths and pulse heights of a plurality of pulses;

multiplying the data vector and a classification matrix, wherein the classification matrix is generated through a machine learning process trained using a plurality of air samples respectively containing a plurality of different types of pollutants, and the classification matrix encodes data regarding local particulate data, local gas data, and contextual Internet data for the plurality of different types of pollutants; and classifying the pollutant based on a result of the multiplying of the data vector and the classification matrix.

\* \* \* \* \*